(12) United States Patent
Geyer

(10) Patent No.: US 8,245,565 B2
(45) Date of Patent: Aug. 21, 2012

(54) SLURRY TRANSPORT AND STORAGE SYSTEM

(75) Inventor: Stefan Geyer, Dresden (DE)

(73) Assignee: Infineon Technologies AG, Neubiberg (DE)

( * ) Notice: Subject to any disclaimer, the term of this patent is extended or adjusted under 35 U.S.C. 154(b) by 742 days.

(21) Appl. No.: 12/131,936

(22) Filed: Jun. 3, 2008

(65) Prior Publication Data

US 2009/0293593 A1 Dec. 3, 2009

(51) Int. Cl.
*G01N 11/04* (2006.01)
(52) U.S. Cl. .............. 73/54.04; 73/54.05; 73/54.11
(58) Field of Classification Search .......... 73/54.04, 73/54.05, 54.11
See application file for complete search history.

(56) References Cited

U.S. PATENT DOCUMENTS

| | | | | |
|---|---|---|---|---|
| 1,635,281 A * | 7/1927 | Larson | | 73/54.11 |
| 1,869,718 A * | 8/1932 | Smith | | 73/54.11 |
| 3,520,179 A * | 7/1970 | Reed | | 73/54.04 |
| 3,952,577 A * | 4/1976 | Hayes et al. | | 73/54.04 |
| 4,221,073 A * | 9/1980 | Malczewski | | 446/267 |
| 4,454,751 A * | 6/1984 | Matta et al. | | 73/54.11 |
| 4,794,787 A * | 1/1989 | Gordon | | 73/54.12 |
| 4,932,242 A * | 6/1990 | Kawashima et al. | | 73/54.07 |
| 4,942,759 A * | 7/1990 | Beers | | 73/54.12 |
| 2003/0182868 A1 * | 10/2003 | Nojo et al. | | 51/307 |
| 2006/0266736 A1 * | 11/2006 | Tregub et al. | | 216/84 |

* cited by examiner

*Primary Examiner* — Lisa Caputo
*Assistant Examiner* — Punam Roy
(74) *Attorney, Agent, or Firm* — Infineon Techn. AG; Philip H. Schlazer

(57) ABSTRACT

An embodiment of the present invention is a transport and storage system for a slurry comprising: a main container; and a test container, the main container and the test container being exposed to the same environmental conditions, the main container and the test container containing a slurry from the same batch, wherein the test container is designed to determine the viscosity of the slurry.

8 Claims, 1 Drawing Sheet

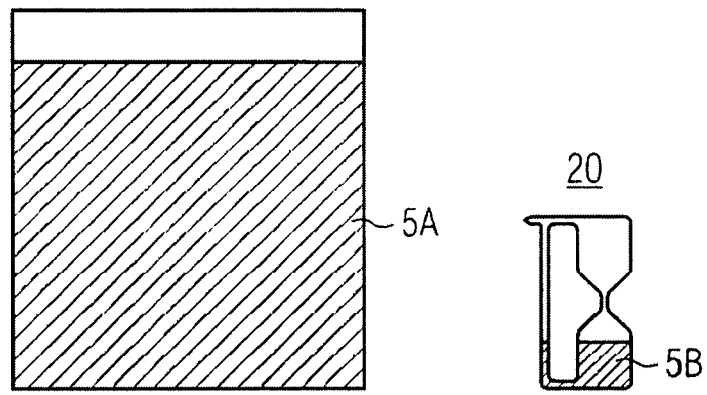
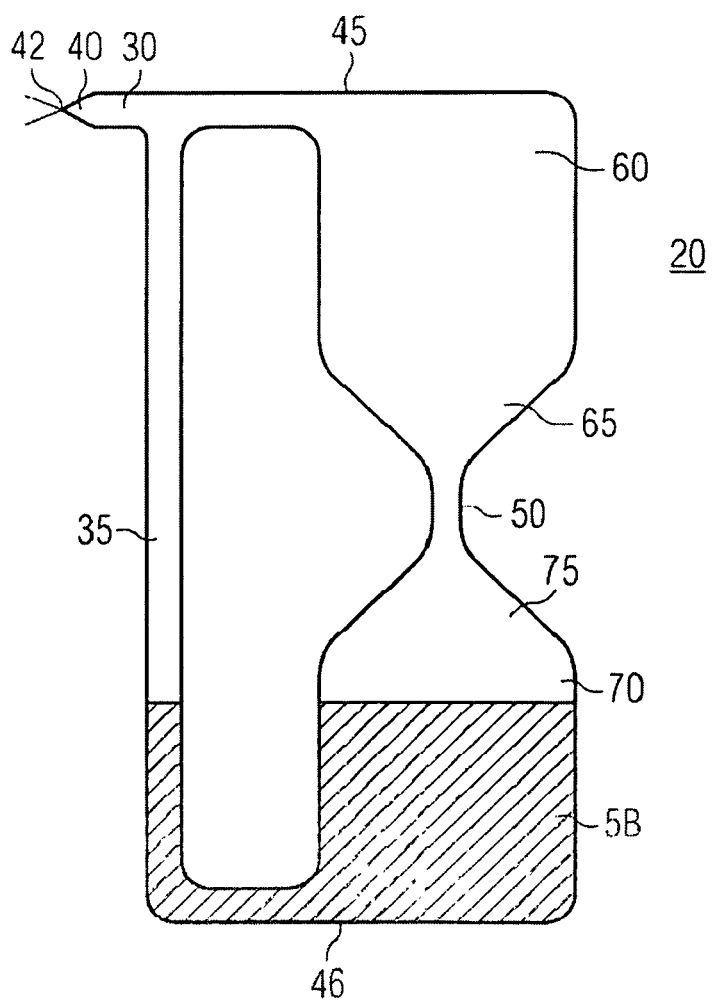

SLURRY TRANSPORT AND STORAGE SYSTEM

FIELD OF THE INVENTION

The present invention relates to slurrys, and, in particular, to slurry transport and storage systems.

BACKGROUND OF THE INVENTION

In the manufacture of integrated circuits, planarization of semiconductor wafers is becoming increasingly important as the number of layers used to form integrated circuits increases. For instance, metallization layers that provide interconnections between various devices may result in nonuniform surfaces. The surface nonuniformities may interfere with the optical resolution of subsequent photolithographic steps, leading to difficulty with printing high resolution patterns. The surface nonuniformities may also interfere with step coverage of subsequently deposited metal layers and possibly cause open or short circuits.

Various techniques have been developed to planarize the top surface of a semiconductor wafer.

One of these techniques involves polishing the wafer using polishing slurry that includes abrasive particles mixed in a suspension agent. Chemical mechanical polishing or planarization (CMP) is a technique of polishing materials including semiconductor substrates and films overlying such substrates, which provides a high degree of uniformity and planarity. The process is used to remove high elevation features on films created during the fabrication of a microelectronic circuitry on the substrate, or to remove a layer of film to reveal the circuitry buried underneath the film. In some cases, the process can planarize semiconductor slices prior to the fabrication of microelectronic circuitry thereon.

A CMP slurry serves multiple roles; namely, it is the medium in which the abrasive particles is dispersed, and secondly it furnishes the chemical agents which promote the chemical process. In order for optimum results in CMP processing, there must be a synergistic relationship between the chemical and mechanical processes.

With this approach, the wafer is mounted on a wafer holder, a polishing pad coated with the CMP slurry is mounted on a platen, the pad and the wafer are rotated such that the wafer provides a planetary motion with respect to the pad, and the polishing pad is pressed against an exposed surface of the wafer with a hydrodynamic layer of the slurry there between. The polishing erodes the wafer surface, and the process continues until the wafer is largely flattened.

Chemical-mechanical polishing has become a popular wafer planarization technique. For instance, chemical-mechanical polishing is becoming a preferred method of planarizing tungsten interconnects, vias and contacts, and with proper process parameters has shown significantly improved process windows and defect levels over standard tungsten dry etching.

The slurry is prepared to the desired composition, the desired concentration, the desired purity, etc. Typically, the slurry is mixed in bulk by adding the abrasive particles and additives, oxidizers, etchants and/or de-ionized water to the suspension agent by a slurry manufacture. The slurry may be fabricated at remote locations from the end use facility.

Containers are employed as a source of process the slurry. In such containers the slurry is transported to the point of use by truck, rail or air transport. At the semiconductor facility the slurry containers are deposited or the slurry is transferred from the containers to a slurry distribution system or deposited in a separate storage tank.

However, the method of transporting or storing the slurry for polishing in a container or other device has, among others, the following three problems (a) though (c):

(a) The slurry may dry or inorganic particles in the slurry may flocculate or precipitate during the transport or storage. As a result the concentration and purity of the slurry or the particle size of the inorganic particles in the slurry may differ from those immediately after the preparation, and the desired polishing characteristics may not be obtained. If the slurry has changed its desired polishing characteristic and is used in the planarization process, this can cause to insufficient planarization results. Nonuniform surfaces on the wafer may lead to faults in the circuitry in one of the following process steps. As a result the scrap rate will increase. Very high costs will arise to semiconductor manufacturers by using such altered slurry.

(b) The desired polishing characteristics depend on the type, etc. of the semiconductor devices, etc. to be polished. For this reason, it is necessary to determine the composition, concentration, purity, pH, etc. of the slurry according to the object to be polished. However, it takes the slurry manufacturers very high cost to manufacture the slurry to the composition, concentration, purity, pH, etc. specified by the manufacturers who manufacture and polish semiconductor devices in their orders and supply the same to the manufacturers who manufacture and polish semiconductor devices on the other hand, a method of supplying the slurry prepared to the specified polishing characteristics (compositions, concentrations, purities, pHs, etc.) to the manufacturers who manufacture and polish semiconductor devices for their stock has a problem that the storage period may be longer and the above-described problem (a) may occur.

(c) The slurry which is low in stability is subject to quality deterioration during the storage or transport. Therefore, even if the polishing characteristics of the slurry has high polishing performance immediately after the manufacture, the quality of the slurry may deteriorate during the storage or transport, the polishing performance of the slurry may also deteriorate, and as a result, the slurry may no longer applicable to any industrial uses.

SUMMARY OF THE INVENTION

An embodiment of the invention is a transport and storage system for a slurry comprising: a main container; and a test container, the main container and the test container being exposed to the same environmental conditions, the main container and the test container containing a slurry from the same batch, wherein the test container is designed to determine the viscosity of the slurry.

An embodiment of the invention is a container for holding a slurry, comprising: a first chamber, a second chamber and a tube fluidly coupling the first chamber to the second chamber, wherein the container is designed to determine the viscosity of the slurry.

An embodiment of the invention is a method for storing or transporting a slurry, comprising: placing a first portion of the slurry in a main container, placing a second portion of the slurry in a test container, wherein the main container and the test container being exposed to the same environmental conditions and determining the viscosity of the slurry in the test container after placing the slurry into the test container.

An embodiment of the invention is a method of determining the condition of a CMP slurry, comprising: determining a first viscosity of the slurry at a first time before storage or transport of the slurry and determining a second viscosity of the slurry at a second time during or after the storage or the transport.

BRIEF DESCRIPTION OF THE DRAWINGS

FIG. 1 shows an embodiment of a transport and storage systems of the present invention; and FIG. 2 shows an embodiment of a test container of the present invention.

DETAILED DESCRIPTION OF THE INVENTION

This invention provides a slurry transport and storage system, and more particularly a slurry transport and storage system comprising a main container and a test container, wherein the test container is designed to be able to determine the viscosity of the slurry.

Main containers are employed to either store a slurry at a fixed location or to transport the slurry from one point to another. A slurry may be transported from one point to another by any means, including but not limited to truck, rail or air. After a slurry is transported to its destination, the slurry may be stored for an indefinite period of time within the main container. Alternatively, at least a portion of the slurry may be transferred from the main container to a slurry distribution system or to another separate storage tank.

The characteristics of slurries may change over time, with or without changes in the external environmental conditions. Desired characteristics (such as composition, concentration, purity, etc.) may vary with time and there is a risk that such characteristics will change when a slurry is either stored for a long period of time or when a slurry is transported over long distances or under changing environmental conditions. Very high costs may arise if the altered slurry is, used for further processes. Hence, it may be useful to provide means to do simple quality tests during and after transportation or storage to determine whether or not the slurry has been altered (and possibly no longer useful for its intended purpose).

One way of determining whether or not a slurry has been altered is to determine its viscosity. If a characteristic of the slurry (for example, its composition, concentration, purity, etc.) has changed, the viscosity may also change.

In an embodiment, the viscosity of a fluid may be calculated using Poiseuille's law. This is the physical law concerning the voluminal laminar stationary flow φ of an incompressible uniform viscous liquid (so called Newtonian fluid) through a cylindrical tube with constant circular cross-section. Poiseuille's law is also sometimes called the Hagen-Poiseuille law. Poiseuille's law was experimentally derived in 1838 and formulated and published in 1840 and 1846 by Jean Louis Marie Poiseuille. Poiseuille's law may be expressed in the following form:

$$\Phi = \frac{dV}{dh} = \frac{\pi \cdot R^4}{8\eta} \cdot \frac{\Delta P}{L} \quad (1.0)$$

where V is a volume of the liquid, poured in the time unit t, v the mean fluid velocity along the length of the tube, x the direction of flow, R the internal radius of the tube, ΔP the pressure difference between the two ends, η the dynamic fluid viscosity, and L the total length of the tube in the x direction.

The dynamic fluid viscosity η can be calculated in the following form:

$$\eta = \frac{\pi \cdot R^4}{\Phi \cdot 8} \cdot \frac{\Delta P}{L} \quad (2.0)$$

One embodiment of the invention is to store or transport slurry in two different types of containers. A main container is used to store or transport the bulk of the slurry. A second and separate test container is used to test the slurry. That is, the test container may be used to provide a way of determining whether or not the slurry stored in the main container has changed during storage or transport.

An embodiment of the present invention is shown in FIG. 1. FIG. 1 shows an example of a main container 10 and a test container 20. In the embodiment shown, the volume of the test container 20 is smaller than the volume of the main container 10. The main container 10 contains a slurry 5A and the test container 20 contains a slurry 5B. In one or more embodiments, the slurry 5A and the slurry 5B are the same slurry. In one or more embodiment, the slurry 5A and slurry 5B are from the same production batch.

Generally, the slurry 5A,B may any type of slurry. An example of a type of slurry which may be used is a CMP slurry, usable for the chemical mechanical polishing or planarization (CMP) process for polishing materials including semiconductor substrates and wavers. In one or more embodiments, the slurry used may be a suspension. The suspension may include solid particles. In one or more embodiments, the particles may have a diameter between about 30 nm and 500 nm. In one or more embodiments, the particles may have a diameter greater than about 40 nm. In one or more embodiments, the particles may have a diameter greater than about 50 nm. In one or more embodiments, the particles may have a diameter less than about 400 nm. In one or more embodiments, the particles may have a diameter less than about 300 nm. In one or more embodiments, the suspension may be a CMP slurry.

During storage and transportation, the main container 10 as well as the test container 20 may be exposed to the same environmental conditions (for example, both containers may be exposed to the same temperature, humidity, etc). By exposing the slurry 5A and the slurry 5B to the same conditions, it is likely that any change in the slurry 5A will also occur in the slurry 5B. Hence, testing the characteristics of the slurry 5B in the test container 20 should be sufficient to determine the characteristics of the slurry 5A in the main container 10 without having to directly test the slurry 5A in the main container 10 (which could be a difficult process).

As noted above, the volume of the test container 20 may be smaller than the volume of the main container 10. This makes testing the slurry easier since the smaller test container 20 is easier to handle than the larger main container 10.

The test container 20 may be adapted or designed so that the test container 20 may be used to determine a characteristic of the slurry 5B. In one or embodiments, the test container 20 is designed or adapted to determine the viscosity of the slurry 5B contained within the container.

To make sure that the main container 10 and the test container 20 are transported and/or stored under the same environmental conditions, the test container 20 may be attached to the main container 10 by suitable attachment means. In an embodiment, the two containers may be attached during storage and/or transportation. The two containers may be removably attached such that the two containers are attached during storage or transport, but may then be separated when the slurry 5B in the test container 20 is tested. In another embodiment, it is possible that the test container be permanently or irremovably attached.

In the embodiment shown in FIG. 1, there is only a single main container 10 and a single test container 20. However, more generally, that may be one or more main containers. Likewise, there may be one or more test containers. In one embodiment, there may be two or more main containers. In one embodiment, there may be two or more test containers.

It is noted that the main container 10 and the test container 20 may be a container which is suitable for storage and transportation of a slurry. In one or more embodiments, the main container 10 and/or the test container 20 may be formed from a metal, a glass or a plastic (such as a polyethylene material). In one or more embodiments, the test container 20 may be made at least partially from a transparent material. Examples of transparent materials include, but not limited to, a glass or a plastic (for example, a polyethylene).

The main container 10 may be removably sealed so that the slurry can be removed when desired. In one or more embodiments, the ratio of the volume of the main container 10 to the test container 20 may be at least 10 to 1.

FIG. 2 shows an example of a test container 20. The test container 20 comprises a first chamber 60 and a second chamber 70 which is fluidly coupled to the first chamber. In the embodiment shown, the coupling is through a tube 50. However, it may also be possible to couple the first chamber to the second chamber without the use of an extra tube.

In an embodiment, the first chamber 60 comprises a funnel portion 65 that tapers from a wide end to an opening at a narrow end. Likewise, the second chamber 70 also comprises a funnel portion 75 that tapers from a wide end to an opening at a narrow end. The opening at the narrow end of the first funnel portion is fluidly coupled to the opening at the narrow end of the second funnel portion through a tube 50. In one or more embodiments, the tube 50 may be a capillary tube. In an embodiment, it is possible that the first chamber consists essentially of the funnel portion. Likewise, in an embodiment, it is also possible that the second chamber consists essentially of the funnel portion.

With regards to tube 50, it is possible that a slurry 5B moving through the tube 50 moves at different speeds depending upon its distance from the center of the tube 50. For example, it is possible that a slurry moves fastest at the center of the tube and slowest at the walls of the tube where the slurry contacts the walls of the tube and is thus slowed by friction. In one or more embodiments, the diameter and/or the length of the tube 50 may be determined in a manner that guarantees a continuous flow of the slurry 5B. In another embodiment, the diameter and/or the length of the tube 50 may be chosen so that the flow through the tube is a drip. In one or more embodiments, the diameter of the tube 50 may be between 0.1-8 mm. In one or more embodiments, the diameter of the tube 50 may be between 0.1-5 mm. In one or more embodiments, the diameter of the tube 50 may be between 0.1-3 mm. In one or more embodiments, the diameter of the tube 50 may be between 0.1-2 mm. In one or more embodiments, the diameter of the tube 50 may be greater than 0.5 mm. The diameter of the tube 50 may depend upon the viscosity of the slurry 5B. In one or more embodiments, the length of the tube 50 may be between about 1-8 mm. In an embodiment, the tube 50 may be a capillary tube.

In one or more embodiments, the diameter of the tube 50 may be chosen so that the volume of slurry can fall through the tube from the top chamber to the bottom chamber of the test container within a time period of about 60 seconds or less. In one or more embodiments, the diameter of the tube 50 may be chosen so that the volume of slurry can fall through the tube from the top chamber to the bottom chamber of the test container within a time period of about 45 seconds or less. In one or more embodiments, the diameter of the tube 50 may be chosen so that the volume of slurry can fall through the tube from the top chamber to the bottom chamber of the test container within a time period of about 30 seconds or less.

In one embodiment, the test container 20 comprises a first supporting stand 45 and a second supporting stand 46 which are located opposite from each other on the upper respectively bottom side of the test container 20 so that the test container 20 can stand on a flat surface such as a floor or table. The first supporting stand 45 may be attached to the first chamber 60 or may be formed as part of it. The second supporting stand 46 may be attached to the second chamber 70 or may be formed as part of it. In the embodiment shown, the first supporting stand 45 and the second supporting stand 46 are perpendicular to the tube 50, however, other shapes are possible.

The test container 20 may further comprise an air compensation tube 35. In the embodiment shown in FIG. 2, the air compensation tube is fluidly coupled between the first chamber 60 and the second chamber 70. The compensation tube 35 may help ensure that a steady flow of the slurry occurs from one chamber to the other.

In order to determine the viscosity of the slurry a defined amount of the slurry 5B may first be placed into the test container 20 through an input opening 30. After a period of time, the slurry 5B will settle into the second chamber 70 as well as in a lower portion of the air compensation chamber. In an embodiment, the slurry 5B may fill about one third to about one half of the volume of the second chamber 70.

After the slurry 5B is added to the test container, the opening 40 may then be closed with a seal 42 so that the test container 20 is fluidly tight (hence, so that the slurry will not leak from the container). The seal 42 of opening 40 may be accomplished in many ways. In one embodiment, the opening 40 may be removeably sealed such that the seal 42 may be removed. This may be done with, for example, a plug. That is, seal 42 may be a plug. In another embodiment, the opening 40 may be irremovably sealed such that the slurry 5B cannot be removed without either breaking the seal 42 or without breaking the test container 20. An example of an irremovable seal would be a wax seal. This may be done to ensure that the container is "tamper free" and that the slurry 5B cannot be removed without knowledge.

After the slurry 5B is added to the test container 20, the viscosity of the slurry 5B may be determined any time. Normally the slurry 5B is in the lower chamber (FIG. 2: second chamber 70) of the test container 20 which is below the empty upper chamber (FIG. 2: first chamber 60). The test container 20 may then be flipped upside down so that the filled second chamber 70 is above the empty first chamber 60. Then, due to gravity, the slurry 5B will flow from the filled second (upper) chamber 70 through the tube 50 into the first (lower) chamber 60 In an embodiment, as noted above, the diameter and the length of the tube 50 may be chosen so that the flow of the slurry 5B through the tube 50 is a drip. In another embodiment, the diameter of the tube 50 may be chosen so that the flow of the slurry 5B is continuous.

As an example, the viscosity of the slurry 5B inside the test container 20 can be determined by measuring the time it takes for a predetermined volume of the slurry 5B to flow from the upper chamber through the tube 50 into the lower chamber (this correspond to the voluminal laminar stationary flow $\phi$) and by using a formula such as the equation 2.0, mentioned above.

As another example, a change in the slurry 5B can be determined by comparing a first viscosity value or a first voluminal laminar stationary flow $\phi_1$ measured before the transport or storage of the slurry 5B with a second viscosity value or a second voluminal laminar stationary flow $\phi_2$ measured during or after the transport or storage of the slurry 5B.

In an embodiment the test container 20 may have a scale for determining the volume of slurry 5B that has flowed from the upper chamber through the tube 50 into the lower chamber.

The flow time depends on many factors such as the diameter and length of the tube 50, the material of the test container 20 as well as the viscosity of the slurry 5B. The air compensation tube 35 may help to ensure that the flow of the slurry 5 from the upper chamber to the lower chamber occurs at a steady or even rate.

In one or more embodiments, the test container 20 may be about 5-20 cm high. These dimensions allow it to handle the test container easily.

It is understood, therefore, that this invention is not limited to the particular embodiments disclosed, but it is intended to cover all modifications which are within the scope and spirit of the invention as defined by the appended claims.

What is claimed is:

1. A method for storing or transporting a slurry, comprising:
   placing a first portion of a slurry in a main container;
   placing a second portion of said slurry in a test container, said main container and said test container being exposed to the same environmental conditions; and
   determining the viscosity of said slurry in said test container after placing said slurry into said test container, wherein said determining said viscosity comprises allowing said slurry to flow from a first chamber of said test container to a second chamber of said test container, wherein said test container is sealed so that the slurry inside said test container cannot be removed without breaking the seal or without breaking said test container.

2. The method of claim 1, wherein said determining said viscosity comprising allowing said slurry to flow through a capillary tube.

3. The method of claim 1, wherein said flow is continuous.

4. The method of claim 1, wherein the volume of said main container is larger than the volume of said test container.

5. The method of claim 1, wherein said slurry is a chemical mechanical polishing (CMP) slurry.

6. The method of claim 1, wherein said test container is attached to said main container.

7. The method of claim 6, wherein said test container is removably attached to said main container.

8. The method of claim 6, wherein said test container is irremovably attached.

* * * * *